United States Patent
He et al.

(10) Patent No.: US 7,257,365 B2
(45) Date of Patent: Aug. 14, 2007

(54) SERUM BIOMARKERS OF HEPATITIS B VIRUS INFECTED LIVER AND METHODS FOR DETECTION THEREOF

(75) Inventors: Qing-Yu He, Sai Ying Pun (HK); Jen-Fu Chiu, Pokfulam (HK); George Lau, Hong Kong (HK); Yuan Zhou, Ap Lei Chau (HK)

(73) Assignee: The University of Hong Kong (HK)

( * ) Notice: Subject to any disclaimer, the term of this patent is extended or adjusted under 35 U.S.C. 154(b) by 213 days.

(21) Appl. No.: 10/831,939

(22) Filed: Apr. 26, 2004

(65) Prior Publication Data

US 2004/0214164 A1  Oct. 28, 2004

Related U.S. Application Data

(60) Provisional application No. 60/465,655, filed on Apr. 25, 2003.

(51) Int. Cl.
*C12Q 1/10* (2006.01)
*C12N 7/00* (2006.01)

(52) U.S. Cl. .......................... 434/5; 435/235.1; 435/193

(58) Field of Classification Search ...................... None
See application file for complete search history.

(56) References Cited

OTHER PUBLICATIONS

Berggren K. et al "Background-free, high sensitivity staining of proteins in one- and two-dimensional sodium dodecyl sulfate-polyacrylamide gels using a luminescent ruthenium complex". Electrophoresis. Jul. 2000;21(12):2509-21.*
Steel L et al. "A proteomic approach for the discovery of early detection markers of hepatocellular carcinoma", Dis Markers. 2001;17(3):179-89. Review.*
Huang W & Gong FY "Diagnostic value of serum biochemical markers for liver fibrosis in patients with hepatitis B virus." Di Yi Jun Yi Da Xu Xu Bao Nov. 2002,; 22(11). Abstract.*
Gong Fy, Huang W.; *Diagnostic Value of Serum Biochemical Markers for Liver Fibrosis in Patients with Hepatitis B. Virus*;PMID: 12433643 [PubMed—indexed for MEDLINE] (2002)22:1034-6.
Berggren, Kiera et al.; *Background-free, High Sensitivity Staining of Proteins in One-and Two Dimensional Sodium Dodecyl Sulfate-Polyacrylamide Gels Using a Luminescent Ruthenium Complex*; Electrophoresis 21 (2000) 2509-2521.
Steel, Laura F. et al.; *A Proteomic Approach for the Discovery of Early Detection Markers of Hepatocellular Carcinoma*; Disease Markers 17 (2001) 179-189.
Chen, Chien-Jen et al.; *Towards Control of Hepatitis B in the Asia-Pacific Region*; Journal of Gastroenterology and Hepatology (2000) 15 (Suppl.) E3-E6.
Feitelson, M.A.; *The Pathogenesis of Chronic Hepatitis B Virus Infection*; Bull. Inst. Pasteur 96 (1998) 227-236.
Chen, Henry Lik-Yuen; *Changing scene in Hepatitis B Serology Interpretation*; Hospital Medicine, January 63 (2002) No. 1.
Lau, George KK; *Hepatitis B. Infection in China*; Clinics in Liver Disease vol. 5 No. 2 May 2001.
He, Qing-Yu, et al.; *Serum Biomakers of Hepatitis B Virus Infected Liver Inflammation: A Proteomic Study*; Proteomics 3 (2003) 666-674.
Buendia, MA; *Hepatitis B Viruses and Cancerogenesis*; Biomed & Pharmacother 52 (1998) 34-43.

* cited by examiner

*Primary Examiner*—Bruce R. Campell
*Assistant Examiner*—Bo Peng
(74) *Attorney, Agent, or Firm*—Robert D. Katz; Cooper & Dunham LLP

(57) ABSTRACT

The invention provides a method for detecting the presence of altered serum proteins in an Hepatitis B Virus (HBV)-infected patient with liver inflammation, comprising: obtaining a sample of serum from the patient; subjecting the sample to protein gel electrophoresis to separate proteins contained therein; staining proteins separated on the electrophoresis gel with silver nitrate solution; scanning the images of stained proteins into an image analysis scanner to obtain gel images; comparing the gel images to control samples of electrophoresis gels prepared from serum of normal patient and serum of HBV-infected patient with liver inflammation to determine whether the sample of serum from the patient contains specific serum proteins. This invention also provides serum protein biomarkers for the diagnosis of patients with HBV infection and liver inflammation.

1 Claim, 5 Drawing Sheets

SERUM BIOMARKERS OF HEPATITIS B VIRUS INFECTED LIVER AND METHODS FOR DETECTION THEREOF

This application claims priority of U.S. Provisional Application No. 60/465,655, filed Apr. 25, 2003, the contents of which are hereby incorporated by reference into this application.

BACKGROUND OF THE INVENTION

Hepatitis B virus (HBV), a serious infectious and widespread human pathogen, represents a major health problem worldwide. Chronic HBV infection has a very high risk of evolving into hepatocellular carcinoma. Although considerable progress was made during the past several years, the pathogenesis of HBV infection is still elusive and a definite diagnosis of HBV-infected liver information still relies on biopsy histological test.

Hepatitis B virus (HBV) infection is one of the most common viral infections in humans with approximately 2 billion people infected [1]. Among them, 350 million became chronically infected. This is of particular concern in Asia-Pacific areas such as Southern China [2]. Around 25-40% will eventually die of liver disease (viz. cirrhosis with or without hepatocellular carcinoma); the death rate being 50% for males and 15% for females. Epidemiological studies reveal that HBV infection is a complicated condition and the pathogenesis of the infection is still not fully defined [2, 3]. Although many HBV markers such as hepatitis B surface antigen (HBsAg), hepatitis B surface antibody, hepatitis Be antigen, hepatitis Be antibody, hepatitis B core antigen, hepatitis B core antibody, IgM and IgG have been identified and used in diagnosing and monitoring the progress of disease, no single serological test can unequivocally diagnose the infection [4]. For example, positive HBsAg is a hallmark for HBV, but negative HBsAg cannot exclude HBV infection [4]. Up to now, a definite diagnosis of HBV-infected liver inflammation still relies on a combination of serological, biochemical and histological examination.

Presently two classes of drugs are used for the treatment of chronic HBV [5, 6]. The first is a class of immunomodulators that act by modulating the immune response of the host to the HBV antigens. The second is a class of viral suppressors. The current best immune modulating drug, interferon α2b, only has limited effectiveness, especially with Asian patients. The viral suppressing agents need to take a long time to effectively decrease the level of HBV. Obviously, more specific and effective diagnosis and treatment methods are needed.

SUMMARY OF THE INVENTION

This invention provides a method for detecting the presence of Hepatitis B Virus (HBV) infection in a patient having liver inflammation, comprising: obtaining a sample of serum from the patient; subjecting the sample to protein gel electrophoresis to separate proteins contained therein; staining proteins separated on the electrophoresis gel with silver nitrate solution; scanning the images of stained proteins into an image analysis scanner to obtain gel images; comparing the gel images to control samples of electrophoresis gels prepared from HBV negative serum and HBV positive serum to determine whether the sample of serum from the HBV-infected patient contains altered serum proteins.

The invention also provides a serum biomarker for diagnosis of HBV infection and liver inflammation in a patient, wherein the serum biomarker comprises one or more of the following proteins: apolipoprotein A-I (apoA-I), apolipoprotein A-I fragments, haptoglobin β chain, haptoglobin, cleaved β chain, haptoglobin α2 chain, apolipoprotein A-IV (apoA-IV), transthyretin, α 1-antitrypsin, α1-antitrypsin fragments/isoforms, or DNA topoisomerases II (topo-II).

DETAILED DESCRIPTION OF THE PREFERRED EMBODIMENTS

Figure 1:
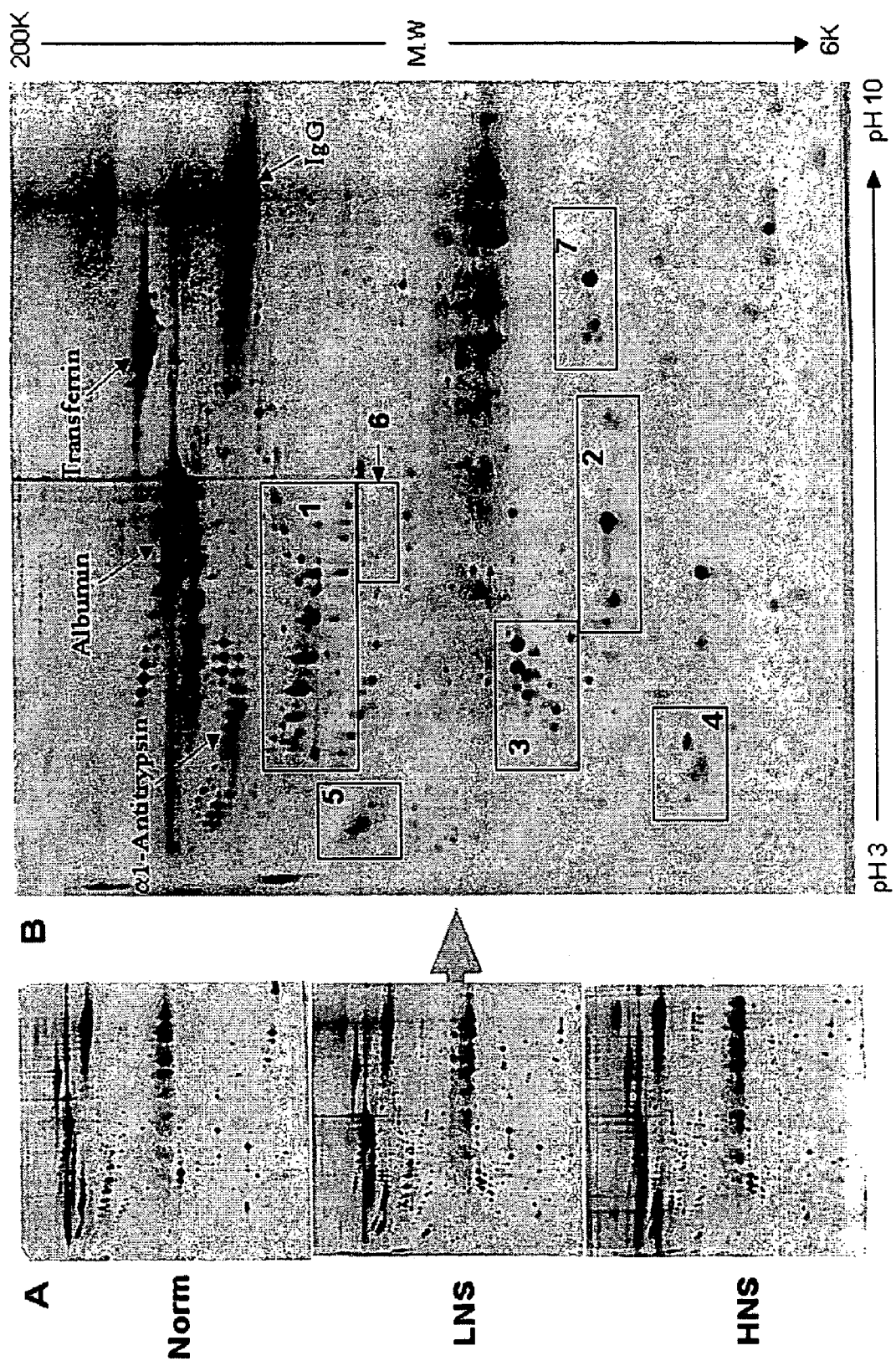
FIG. 1 shows three representative 2D-gel images for normal, LNS and HNS serum samples respectively (A), and an enlarged master LNS gel displaying the common features of human serum proteins (B). (Norm: normal, LNS & HNS: low and high necroinflammatory score).

The invention provides a method for detecting the presence of Hepatitis B Virus (HBV) infection in a patient having liver inflammation, comprising: (a) obtaining a serum sample from the patient; (b) separating the proteins present in the serum sample of the patient in order to determine the presence of biomarkers in the sample; and (c) comparing the proteins present in step (b) with proteins present in control serum samples of normal patients to determine whether the sample of serum from the HBV-infected patients contains altered serum proteins indicative of HBV infection of an inflamed liver.

The invention provides a method for detecting the presence of Hepatitis B Virus (HBV) infection in a patient, comprising: obtaining a sample of serum from the patient; subjecting the sample to protein gel electrophoresis to separate proteins contained therein; staining proteins separated on electrophoresis gel with silver nitrate solution; scanning the images of stained proteins into an image analysis scanner to obtain gel images; and comparing the gel images to control samples of electrophoresis gels prepared from serum of normal patients and serum of patients with HBV-infected and liver inflammation to determine whether the sample of serum from the patient contains altered serum proteins indicative of chronic HBV infection of inflamed liver. Preferably, the sample of patients with HBV infection and liver inflammation contains apolipoprotein A-I (apoA-I), apolipoprotein A-I fragments, haptoglobin β chain, haptoglobin cleaved β-chain, haptoglobin 2 chain, apolipoprotein A-IV (apoA-IV), transthyretin, α1-antitrypsin, α1-antitrypsin fragments/isoforms, or DNA topoisomerases II (topo-II). In another embodiment, this same serum for use in the method contains apolipoprotein A-I or a fragment thereof.

The invention also provides a serum biomarker for diagnosis of an HBV infected liver inflammation in a patient, wherein the serum biomarker comprises one or more of the following identified proteins: apolipoprotein A-I (apoA-I), apolipoprotein A-I fragments, haptoglobin β chain, haptoglobin, cleaved β-chain, haptoglobin 2 chain, apolipoprotein A-IV (apoA-IV), transthyretin, α1-antitrypsin, α1-antitrypsin fragments/isoforms, or DNA topoisomerases II (topo- II). In another embodiment, the serum biomarker contains purified apolipoprotein A-I or a fragment thereof.

The invention will be better understood by reference to the following experimental details, but those skilled in the art will readily appreciate that the specific examples detailed herein are illustrative and are not meant to limit the invention as described herein, which follow thereafter.

EXPERIMENTAL DETAILS

I. Introduction

Proteomic analysis is a powerful technology recently developed to enhance our study on the diagnosis, treatment and prevention of human diseases [7, 8]. By comprehensively examining the different protein expression profiles (expression level, post-translational modification, interaction, etc.) between normal and diseased or drug-treated samples through 2-dimentional electrophoresis or protein chips, proteomics may provide information on new biomarkers, disease-associated targets and the process of pathogenesis. This technique has been extensively employed to investigate cancers and other diseases [9-11] but there is currently no report concerning the proteomic study on HBV infected liver inflammation. In this study, we used proteomics to globally analyze HBV-infected serum samples. By comparing to the normal serum samples, many significantly different protein expressions were identified. Detailed analysis of these proteins may reveal valuable information for the diagnosis and therapy of HBV-infected liver disease.

In this report, we used proteomics technology to globally exam HBV-infected serum samples aiming at searching for liver disease-associated proteins that can be used as serological biomarkers for diagnosis and/or target proteins for pathogenetic study. By comparing with normal and HBV negative serum samples, we found that at least seven proteins were significantly changed in sera of patients with HBV-infection and liver inflammation. These greatly altered proteins were identified to be haptoglobin $\beta$ and $\alpha 2$ chain, apolipoprotein A-I and A-IV, $\alpha 1$-antitrypsin, transthyretin and DNA topoisomerase II$\alpha$. The alteration of these proteins presents not only in their quantities but also in their patterns (or specificity), which can be correlated with the necroinflammatory scores. In particular, apolipoprotein A-I displays heterogonous change in expression level with different isoforms and $\alpha 1$-antitrypsin produces evidently different fragments implying diverse cleavage pathways. These unique phenomena appear specific to HBV infection. A combination simultaneously considering the quantities and isoforms of these proteins could be a useful serum biomarker (or index) for HBV diagnosis and therapy.

II. Materials and Methods

A. Human Subjects

We studied 18 chronic hepatitis Be antigen positive Chinese subjects follow-up at the Hepatology Research Clinic (by GKK Lau), Queen Mary Hospital, Hong Kong SAR, China. Nine were in the immune-tolerant phase (Group 1) and 9 were in the immune-clearance phase (Group 2) (Table 1). They all had a liver biopsy for assessment or for pre-treatment assessment in accordance to the clinical trial protocol [12]. The liver biopsies were assessed by 2 pathologists who were unaware of the patient's clinical findings. Both the histology and the modified histological activity index were assessed [13]. Serum samples collected at the time of liver biopsy were evaluated for serum ALT level and the serum HBV DNA was quantitated by the bDNA signal amplification assay (bDNA Quantiplex™ HBV DNA, Chiron, Emeryville, Calif., USA) [14]. Group 1 patients had high serum HBV-DNA ($6554 \pm 1731 \times 10^6$/ml), low ALT level ($33 \pm 14$ IU/L) and low necroinflammatory scores (LNS) ($\leqq 2$) and group 2 patients had low serum HBV DNA ($922 \pm 1388 \times 10^6$/ml), high ALT level ($427 \pm 253$ IU/L) and high necroinflammatory scores (HNS) ($\geqq 7$) (Table 1). In addition, 5 subjects with hepatitis B negative and ten normal subjects were used as control. All serum samples were stored at $-80°$ C. until use. The protein concentration of all samples was determined by the method of Bradford.

B. 2D-Gel Electrophoresis

The 2D electrophoresis was performed with Amersham Pharmacia IPGphor IEF and Ettan Dalt six electrophoresis units using the protocol suggested by the company of Amersham Pharmacia. Briefly, 250 μg (~3 μl) of serum sample was mixed into 340 μl rehydration solution containing 8 M urea, 4% CHAPS, 1 mM PMSF, 20 mM DTT and 0.5% IPG buffer. Rehydration step was carried out with precast 18 cm IPG strips for more than 10 hours under a low voltage of 30 V. IEF was run following a "step-wise" voltage increase procedure: 500 V and 1000 V for 1 hour each and 5000-8000 V for about 10 hours with a total of 64K Vh. After IEF, the strips were subjected to two step equilibration in the equilibration buffers containing 6 M urea, 30% glycerol, 2% SDS and 50 mM Tris-HCl (pH 6.8) with 1% DTT (w/v) for the first step and 2.5% IAA (w/v) for the second step. The strips were then transferred onto the second-dimensional SDS-PAGE which was run on 1.5 mm thick 12.5% polyacrylamide gels at 10° C.

C. Silver Staining

The gels were fixed in 40% ethanol and 10% acetic acid in water overnight, and then incubated in a buffer solution containing 30% ethanol, 41% sodium acetate and 0.2% sodium thiosulfate for 30 minutes. After washing three times in water for 5 minutes each, the gels were stained in 0.1% silver nitrate solution containing 0.02% formaldehyde for 40 minutes. Development was performed for 15 minutes in a solution consisting of 2.5% sodium carbonate and 0.01% formaldehyde. EDTA solution (1.46%) was used to stop the development and the stained gels were then washed three times in water for 5 minutes each.

D. Image Acquisition and Analysis

The stained gels were scanned in an ImageScanner (Amersham) operated by a software, LabScan 3.00, from Amersham Pharmacia Biotech. Intensity calibration was done with an intensity step wedge prior to gel image capture. Image analysis was carried out using the ImageMaster 2D Elite software 4.01 from Amersham Pharmacia. Image spots were initially detected, matched and then manually edited. Ten gel images of normal serum samples were averaged and set as the reference for comparison. Each spot intensity volume was processed by background subtraction and total spot volume normalization, the resulting spot volume percentage was used for comparison. Only those significant different spots (2-fold increase or decrease) were selected for analysis with mass spectrometry.

E. Tryptic in-Gel Digestion.

Protein spots were excised and transferred into siliconized 1.5 ml Eppendorf tubes. Gel chips were de-stained in a 1:1 mixture solution of 30 mM potassium ferricyanide and 100 mM sodium thiosulfate and then equilibrated in 50 mM ammonium bicarbonate to get pH 8.0. After hydrated with acetonitrile and dried in a SpeedVac, the gels were rehydrated in a minimal volume of trypsin solution (10 μg/ml in 25 mM $NH_4HCO_3$) and incubated at 37° C. overnight. The supernatant was directly applied onto the sample plate with equal amount of matrix. If necessary, the in-gel digests were extracted subsequently with 50% and 80% acetonitrile, and then concentrated and de-salted by Zip tips prior to applying on the sample plate.

F. MALDI-TOF Mass Analysis and Protein Identification

Tryptic peptide mass spectra were obtained using a Voyage-DE STR MALDI-TOF mass spectrometer (Applied Biosystems). The instrument setting was reflector mode with 175 ns delay extraction time, 60-65% grid voltage, and 20 k accelerating voltage. 250 Laser shots per spectrum were used to acquire the spectra with mass range from 600 to 2500 Daltons. The trypsin autolytic fragment peaks (906.5049, 1153.5741 and 2163.0570) serve as internal standards for mass calibration. Protein identification was performed by searching in NCBInr protein database using MS-Fit http://prospector.ucsf.edu/. The criteria for searching were set with 50 ppm or better mass accuracy, at least 4 matching peptide masses and molecular weight and p/matching estimated values from gels. Post-source decay MS/MS measurement and MS-Tag http:H/prospector.ucsf.edu/searching were also performed to confirm the results from the MS-Fit. Species search was limited in *Homo sapiens*.

III. Results

A. Protein Separation

Two groups of HBV-infected serum samples together with control samples were applied to 2D-PAGE and proteins visualized by silver staining. 2D gels were run three times for each sample to minimize gel-to-gel variation. FIG. 1A shows three representative gel images for normal, HBV-infected low and high necroinflammatory score serum (LNS and HNS), respectively. FIG. 1B is an enlarged master LNS gel displaying the common features of human serum proteins. Overall, the gel has a very similar pattern to the plasma map in the SWISS-2D database http://prospector.ucsf.edu/ except lacking fibrinogen. More than 1000 spots were detected in a gel ranging from 6 k to 20 k Da of molecular mass with p/s between 4 and 10. Many trains of spots represent those proteins that have primary structure with different degrees of glycosylation and/or phosphoralation (isoforms), resulting in a progressive change in the p/and molecular weight. Spot volume comparison was made between three types of samples with assistance of the ImageMaster program. Significant and constant differences were found in at least seven areas shown in FIG. 1B.

B. Protein Identification

The protein spots that have significant differences were cut off and subjected to trypsin digestion, MALDI-TOF mass spectra measurement and database searching. Where appropriate, protein identifications were confirmed by comparing spot locations and patterns to those in the SWISS database plasma map. Table 2 summarizes the identified proteins in the seven areas and their alterations among normal, LNS and HNS serum samples. Overall, the expressions of three proteins (groups) are suppressed and five proteins (groups) are enhanced in the sera of patients with chronic HBV-infection and liver inflammation.

Figure 2:
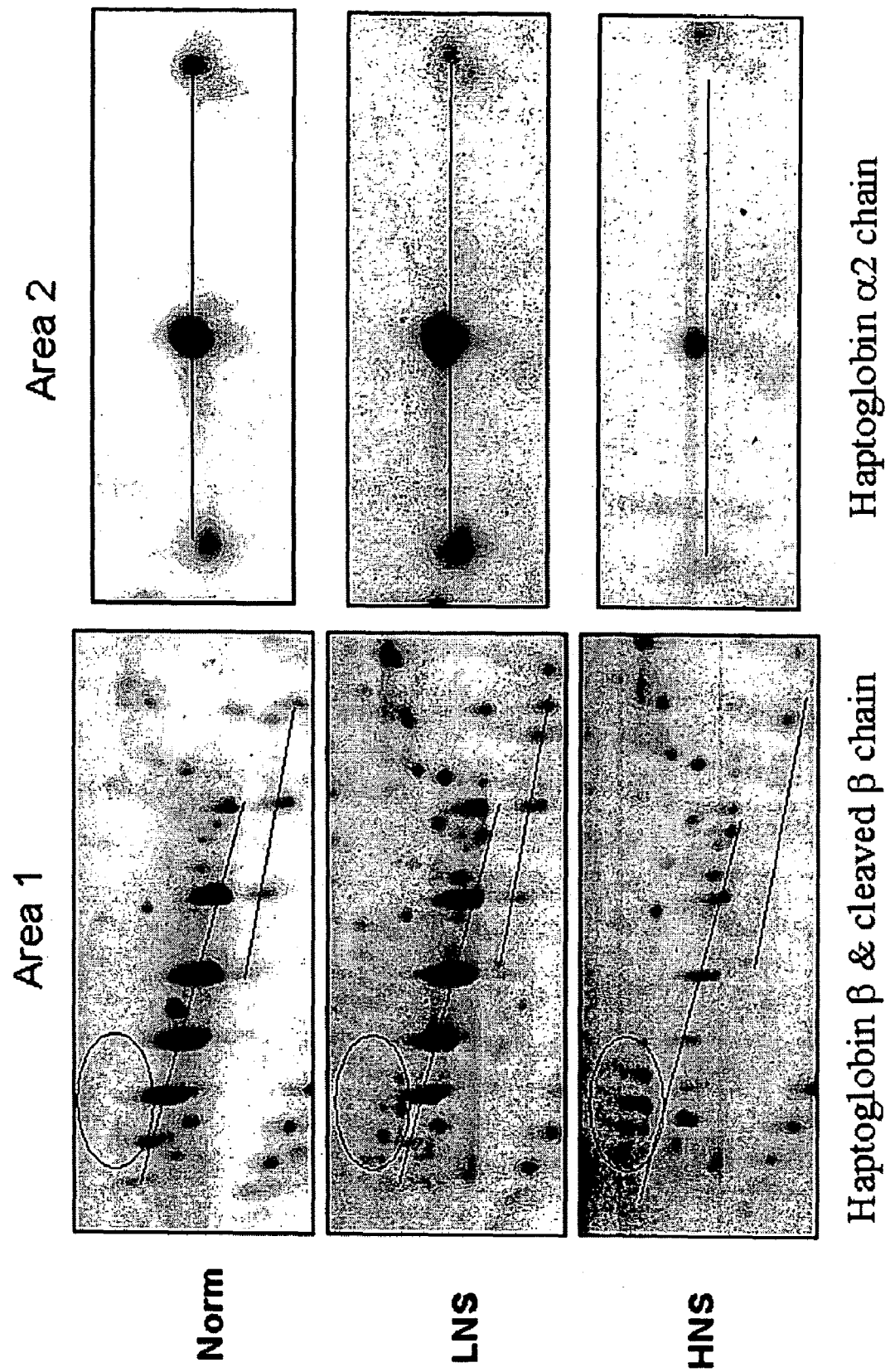
FIG. 2 includes patterns of haptoglobin showing the alterations of the protein in Areas 1 & 2 (Norm: normal, LNS & HNS: low and high necroinflammatory score).

One of remarkable changes is shown in FIG. 2 (Areas 1 & 2 in FIG. 1B) concerning haptoglobin. Haptoglobin α2 chain, β chain and cleaved β chain present their own characteristic train patterns in 2D gels, featuring with three, seven and six detectable isoforms respectively. Compared to that in normal samples, haptoglobin overall slightly increased or had no change in the LNS serum samples but was significantly suppressed in the HNS patients (Table 2). In some cases (30%) the protein was diminished to undetectable level. In contrast, a protein cluster highlighted in circle in the Area 1 of FIG. 2 gradually increases its expression level from undetectable in the control to partially visible in LNS and then to fully appearance in HNS.

Figure 3:
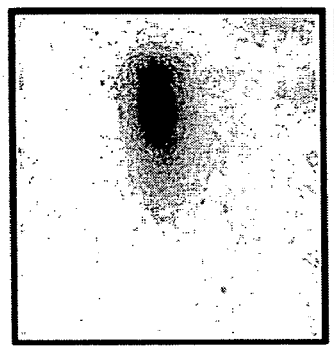
FIG. 3 shows protein alterations in Areas 3 & 4 concerning apoA-I, apoA-IV and transthyretin (TTR) (Norm: normal, LNS & HNS: low and high necroinflammatory score).
Figure 3:
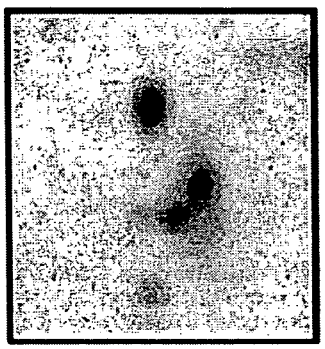
Figure 3:
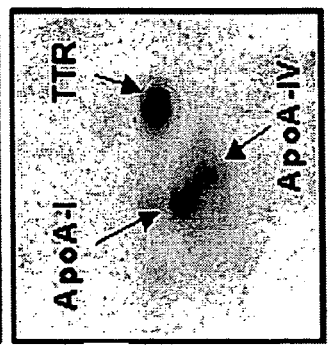
Figure 3:
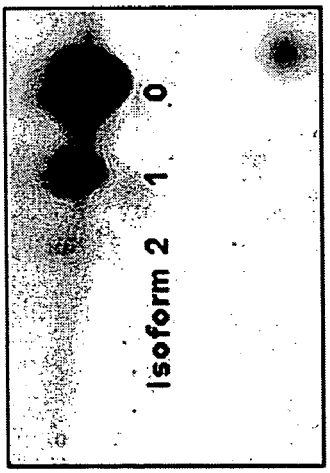
Figure 3:
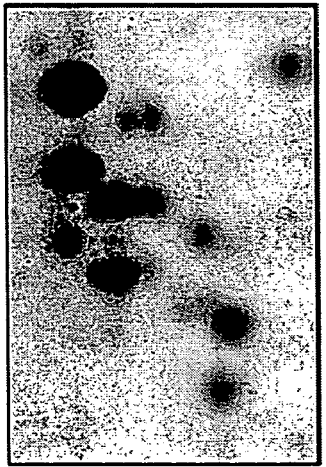
Figure 3:
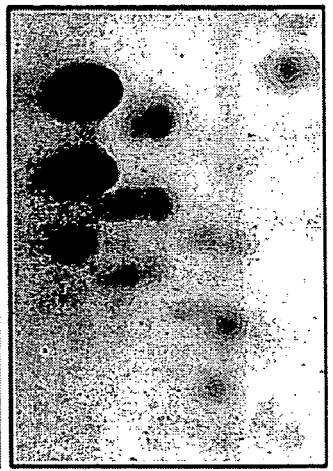

FIG. 3 displays another dramatic change occurring in apolipoprotein A-I (apoA-I) region (Area 3 in FIG. 1B). Normal serum sample has three main apoA-I protein spots (isoforms 2, 1 and 0 from left to right)[15] with one to three very weak cleaved fragment spots immediately below the main spots. In the chronic HBV-infected serum samples, the entire pattern of apoA-I profile was altered. Isoform 2 was significantly up-regulated, isoform 0 was evidently down-regulated, while isoform 1 remained unchanged (Table 2). In addition to the three major spots, the weak fragment spots were significantly enhanced as well as a number of new spots appeared in the low molecular weight area (FIG. 3). These new spots were identified to have the primary sequence of apoA-I and they probably belong to the cleaved fragments of apoA-I or its other isoforms. It is also worth noting that overall the main apoA-I protein spots decrease their volumes in both LNS and HNS samples and the cleaved fragments of apoA-I or other isoforms appear in higher volumes in LNS than those in HNS samples (Table 2).

One more apoA-I fragment was observed in the even low molecular weight Area 4 (FIG. 3). This spot appeared in both LNS and HNS samples but not in the normal serum samples. Similarly in the same Area 4, a spot of apoA-IV was identified in both HBV-infected samples but was undetectable in the control. The only one detectable spot in the Area 4 of normal samples was identified to be transthyretin. The expression level of this transthyretin isoform was apparently decreased in the serum of HBV carriers (Table 2).

Figure 4:
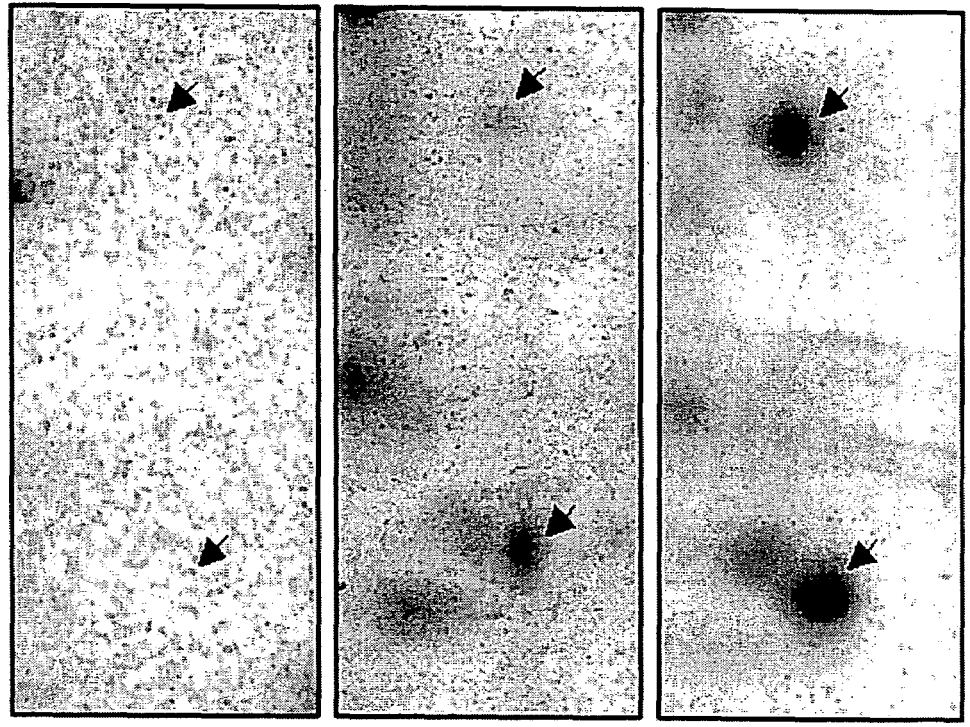
FIG. 4 shows protein alterations in Areas 5 & 6 concerning α1-antitrypsin (Norm: normal, LNS & HNS: low and high necroinflammatory score).
Figure 4:
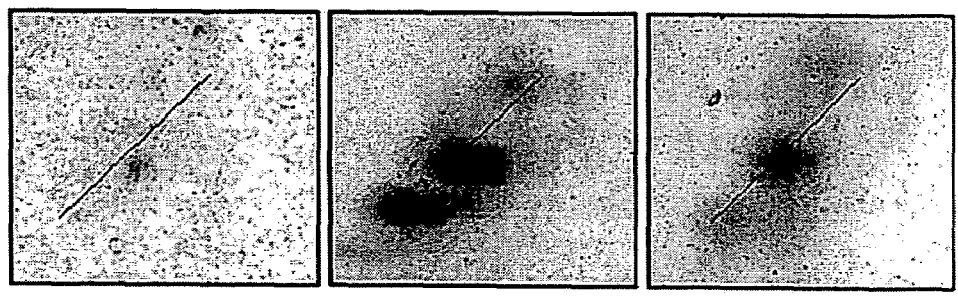

FIG. 4 shows the protein alterations in Areas 5 and 6 in FIG. 1B. Three spots in Area 5 and two spots in Area 6 were markedly intensified in both LNS and HNS samples (Table 2). These spots are identified to have the same primary sequence with α1-antitrypsin. This protein normally appears in a group of spots representing various phenotypes in the 2D gel ranging from p/5.0-5.2, MW 55 kDa http://prospector.ucsf.edu/(FIG. 1B). No significant difference in the level of the normal α1-antitrypsin was found between control and HBV serum samples. However, α1-antitrypsin level in the lower molecular weight areas (MW 38-39 kDa) is greatly enhanced in HBV samples (Table 2). The increased expression level of the protein in the Area 6 is 2-fold more in HNS than that in LNS samples.

Figure 5:
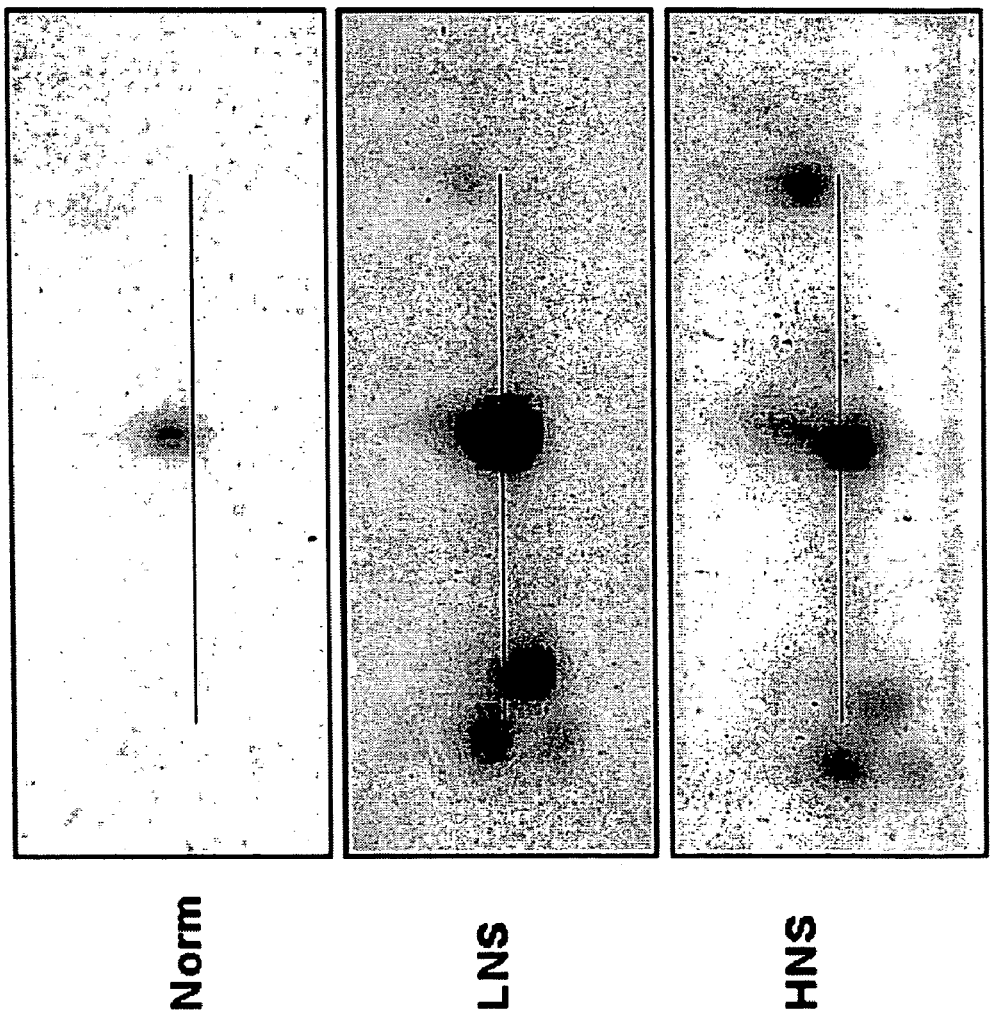
FIG. 5 shows patterns of DNA topoisomerase II β showing the alterations of the protein in Area 7 (Norm: normal, LNS & HNS: low and high necroinflammatory score).

Spots in Area 7 were identified as DNA topoisomerase II (Topo II) (FIG. 5). Only one spot of this protein was detected in the normal serum whereas a group of five spots developed in HBV samples. As a result, the protein level was elevated about 20 fold in total in the HBV serum (Table 2). Given the fact that intact TopoIIβ has a molecular weight of 180 kDa, these spots in Area 7 are probably the low-molecule fragments.

C. Discussion

Haptoglobin, apoA-I and α1-antitrypsin are among most abundant serum glycoproteins secreted by the liver. It is therefore reasonable that liver damage results in alterations of these proteins, which in turn can be used as biomarkers for monitoring the liver diseases. Recent efforts have been made to combine these proteins with other basic serum markers as an index for the diagnosis of HCV disease thus reducing the number of liver biopsies performed in patients with chronic HCV infection [16, 17]. Almost all these studies are based on the comparison of the amount of the marker proteins between normal and diseased samples. The current report examined the alterations of these biomarkers globally (their expression levels and patterns) through proteomic analysis and thus may provide more specific assessments for HBV infection.

Haptoglobin has been long used to study the serum of various liver diseases including HBV infection. However, contradictory results were reported. Earlier studies showed that haptoglobin level were decreased in chronic [18, 19] and acute viral hepatitis. [20], other reports claimed that haptoglobin level changed in acute hepatitis [21] but no significant difference were observed in chronic hepatitis [22]. A more recent study revealed that haptoglobin increased in all acute viral hepatitis and in chronic HBV infection but decreased in patients with other chronic hepatitis [23]. These conflicting results may be due to the different measurements used, samples sources and stages of disease. Here we specifically examined the HBV serum at low (LNS) and high (HNS) inflammatory stages. Our results revealed that both haptoglobin α2 and β chains slightly increased in the LNS serum but significantly decreased in the HNS samples (Table 2). This implies that HBV infection without inflammation may not cause serious liver damage, corresponding to the low ALT and high HBV-DNA immune-tolerant phase in the chronic HBV infection [6]. Meanwhile, advance stage of inflammation causes severe liver function impairment, resulting in the substantial decrease of both haptoglobin α and β chains secreted from the injured liver.

Many studies have shown that the level of apoA-I correlates with changes in the hepatocellular function in chronic liver disease [24-27]. A low level of the protein implies the severity of liver cell injury. It is believed that apoA-I is controlled at posttranslational level [28] and liver damage decreases the apoA-I conversion from other isoforms [29]. Our results indicate that in chronic HBV infection apoA-I alteration occurs not only in its level but its whole pattern in the 2D gel (FIG. 3). In particular, three main apoA-I isoforms change their expression level independently. This is the first time such phenomenon was observed in HBV infection. This heterogeneous alteration reflects different posttranslational control occurring to the different isoforms of apoA-I, which may be correlated with specific features or functions of the isoforms. A further identification of the specific modifications underlying these specific protein isoforms may provide the useful diagnostic information of HBV infection. The appearance of the new cluster of apoA-I spots also appears specific to HBV infection because no similar observation was revealed in other inflammations such as alcoholic, cirrhosis and other liver injury [30] (unpublished results). These new spots may contain the different isoforms of apoA-I that may not be detected by the common assay of nephelometry. This suggests that the observed decrease of apoA-I level in chronic hepatitis only corresponds to the alteration of the three main apoA-I isoforms. It is therefore possible to develop monoclonal antibodies specifically to the apoA-I isoforms for the serological assay of HBV infection. This possibility is under investigation.

Closely linked to apoA-I in a multigene cluster, apoA-IV is a glycoprotein synthesized by the human intestine [31, 32]. ApoA-IV has been suggested to have protective function against lesions and atherosclerosis [33-35] and have physiological role in modulating gastric function [36, 37]. Suppressed level of apoA-IV was found in the cases of inflammation [38], acute hepatitis [39] and cirrhosis [40]. The apoA-IV spot appears in the low molecular weight area of current HBV sera probably is a fragment of the entire protein (~45 kDa). This implies that the observed decrease of apoA-IV is due to the protein cleavage during inflammation, another indicator for the assessment of HBV infection.

Transthyretin, a known negative acute-phase protein, was found to have significantly reduced concentration in various acute liver diseases [23, 41, 42]. We confirmed in the present report that at least one transthyretin isoform displayed a half of its expression level in both LNS and HNS serum samples (Table 2), suggesting liver dysfunction occurs with the virus infection even before serious inflammation.

As one of the powerful inhibitors of apoptosis and caspase activation, α1-antitrypsin can inhibit many of the proteases released from dying cells and thus protects normal tissues during periods of stress such as inflammation [43]. The observed increase of α1-antitrypsin level in both acute and chronic hepatitis [19] may be the response of self-protection of the liver. On the other hand, the deficiency of α1-antitrypsin activity has been shown to closely associate with liver diseases [44, 45]. This α1-antitrypsin deficiency can be inherited from mutant genes in some phenotype variants [46-48]. In the present study we found that α1-antitrypsin increases in the lower molecular weight (~40 kDa) region. Considering the fact that α1-antitrypsin is a single-chain protein of 394 amino acids, 52 kDa, we believe that the lower MW proteins probably are the fragments rather than other phenotypes. Interestingly, these large fragments spread out in two different p/areas, present in totally different patterns, and display different increasing extents between LNS and HNS cases, indicating that these are the products of different cleavage pathways. Further characterization of these peptides may reveal underlying information helpful for understanding HBV infection and for its diagnosis. Moreover, no such particular phenomenon was observed in other liver inflammation, suggesting that the change could be specific to HBV infection.

DNA topoisomerase II is an ATP-dependent enzyme that catalyses topological genomic change by passing one DNA duplex through a transient break in a second duplex [49]. The enzyme has two separately encoded isoforms, topoIIα and topoIIβ. Both forms are molecular targets for several widely used anticancer agents which interrupt enzymatic DNA breakage-reunion, leading to a stop of DNA replication processes and ultimately cell death [50]. The overexpression of topoIIα was suggested to have potential linkage with several aggressive tumors including HCC [51], lung cancer [52, 53] and ovarian cancer [54]. The elevated mRNA level of topoIIβ was also found in human ovarian cancer [54] and K562 cells [55]. The greatly enhanced topoIIβ fragments currently found in HBV sera may reflect the significant increase of topoIIβ expression related to HBV infection. Although whether this alteration represents an initial sign of malignant cell transformation induced by HBV requires more detailed investigation, it may indicate that a DNA metabolic process is involved in HBV infection.

HBV disease is a complicated condition. Many serum biomarkers have been identified and used in clinical diagnosis based on their quantity change. However, different serological tests have various limitations in the diagnosis and management of chronic HBV infection [4]. This study demonstrated that 2D-PAGE electrophoresis can generate a comprehensive serological profile in which the HBV protein biomarkers change patterns not only in their quantities but their qualities (or specificity). In particular, we have observed various alterations occurring with the different isoforms of these biomarkers, which are especially informative and useful for assessing HBV infection. Proteomic analysis provides a specific and suitable alternative to conventional measurements of HBV diagnosis and progression in the clinical research setting. A global examination combining these basic serum markers, together with their special isoform alteration, could be useful in HBV therapy and thus substantially reduces the number of liver biopsies performed in patients with chronic HBV infection.

V. References

The following references, referred to in the specification by numeral, are incorporated by reference herein as background and to provide the state of the art.

[1] Maynard, J. E., Kane, M. A., Alter, M. J., in: Zuckerman, A. J. (Ed) *Control of hepatitis B by immunization: Global perspective.* 1988, pp. 967-969.

[2] Chen, C. J., Wang, L. Y., Yu, M. W., *J. Gastroenterol Hepatol.* 2000, 15(suppl):E3-E6.

[3] Feitelson, M. A., *Bull. Inst. Pasteur.* 1998, 96, 227-236.
[4] Chan, H. L. Y., *Hospital. Med.* 2002, 63, 16-19.
[5] Lai, C. L., Wu, P. C., *Hong Kong Med. J.* 1997, 3, 289-296.
[6] Lau, G. K. K., *Clin. Liver Dis.* 2001, 5, 361-379.
[7] Borman, S., *Chem. Engineering News* 2000, 78, 31-37.
[8] Hunt, D. F., *J. Proteome Res.* 2002, 1, 15-19.
[9] Jungblut, P. R., Zimny-Arndt, U., Stulik, J., Koupilova, K., Pleibner, K-P., Otto, A. et al. *Electrophoresis* 1999; 20:2100-2110.
[10] Hanash S M, Madoz-Gurpide J, Misek D E. Identification of novel targets for cancer therapy using expression proteomics. *Leukemia* 2002; 16:478-485.
[11] Srinivas P R, Srivastava S, Hanash S, Wright Jr G L. *Clin Chem* 2001; 47:1901-1911.
[12] Lau G, Nanji A, Hou J, Fong D, Au W, Yuen S et al. *Viral Hepat* 2002; 9(4):280-287.
[13] Knodell R, Ishak K, Black W, Chen T, Craig R, Kaplowitz N et al. *Hepatology* 1981; i(1):431 -435.
[14] Urdea M, Horn S, Fultz T, Anderson M, Runnings J, Hamren S et al. *Nucleic Acids Res Symp Ser* 1991; 24:197-200.
[15] Contiero E, Ferrari R, Vaselli G M, Folin M. *Electrophoresis* 1997; 18(1):122-126.
[16] Imbert-Bismut F, Ratziu V, Pieroni L, Charlotte F, Benhamou Y, Poynard T. *Lancet* 2001; 357:1069-1075.
[17] Poynard T, Imbert-Bismut F, Ratziu V, Chevret S, Jardel C, Moussalli J et al. *J Viral Hepat* 2002; 9(2):128-133.
[18] Hiramatsu S, Kojima J, Okada T T, Inai S, Ohmori K. *Acta Hepato-Gastroenterologica* 1976; 23(3):177-182.
[19] Meliconi R, Parracino O, Facchini A, Morselli-Labate A M, Bortolotti F, Tremolada F et al. *Liver* 1988; 8(2): 65-74.
[20] Borsotti M, De Philippis C, Leoncini F, Mazzotta F, Paci F, Piazza E et al. *Quad Sclavo Diag Clin Lab* 1980; 16(4):385-401.
[21] Pateva R, Koichev K, Vurbanov G, Rusinov E, Danev I. *Vutreshni Bolesti* 1982; 21(2):65-69.
[22] Henke J, Kellner S, Kasulke D. *Blut* 1978; 36(2):109-110.
[23] Volchkova E V, Pak S G, Malov V A, Umbetova K T. *Ter Arkh* 2000; 72(11):18-21.
[24] Nayak S S, Ramani A, Kamath S S, Kundaje G N, Aroor A R. *Biochem Med Metab Biol* 1988; 40(3):299-304.
[25] Matsuura T, Koga S, Ibayashi H. *Gastroenterol Jpn* 1988; 23(4):394-400.
[26] Geiss H C, Ritter M M, Richter W O, Schwandt P, Zachoval R. *Hepatology* 1996; 24(6): 1334-1337.
[27] SelimoGlu M A, AydoGdu S, YaGci R V. *Pediatr Int* 2002; 44(4):400-403.
[28] Panduro A, Lin-Lee Y C, Chan L, Shafritz D A. *Biochemistry* 1990; 28:8430-8435.
[29] Isobe H, Sakai H, Satoh M, Sakamoto S, Koga S, Nawata H. *Clin Chem Acta* 1990; 189(3):303-311.
[30] Gravel P, Walzer C, Aubry C, Balant L P, Yersin B, Hochstrasser D F et al. *Biochem Biophys Res Comm* 1996; 220:78-85.
[31] Tso P, Liu M, Kalogeris T J, Thomson A B. *Annu Rev Nutr* 2001; 21:231-254.
[32] Vergnes L, Taniguchi T, Omori K, Zakin M M, Ochoa A. *Biochem Biophys Acta* 1997; 134(8):299-310.
[33] Kalopissis A D, Chambaz J. *Int J Tissue React* 2000; 22:67-78.
[34] Ostos M A, Conconi M, Vergnes L, Baroukh N, Ribalta J,. Girona J et al. *Arterioscler Thromb Vasc Biol* 2001; 21:1023-1028.
[35] Duverger N, Tremp G, Caillaud J M, Emmanuel F, Castro G, Fruchart J C et al. *Science* 1996; 274:966-968.
[36] Kalogeris T J, Rodriguez M D, Tso P. *J Nutr* 1997; 12(7):537S-543S.
[37] Vergnes L, Baroukh N, Lehy T, Moizo L, Bado A, Baralle M et al. *FEBS Lett* 1999; 460:178-181.
[38] Quilliot D, Walters E, Guerci B, Fruchart J C, Duriez P, Drouin P et al. *Metabolism* 2001; 50:1019-1024.
[39] Miyata Y, Koga S, Ibayashi H. *Gastroenterol Jpn* 1986; 21:479-485.
[40] Seishima M, Usui T, Naganawa S, Nishimura M, Moriwaki H, Muto Y et al. *J Gastroenterol Hepatol* 1996; 11:746-751.
[41] Yasmin M Y, Aziz B, Nazim M, Madhavan R K. *Malays J Pathol* 1993; 15:147-150.
[42] Citarella F, Felici A, Brouwer M, Wagstaff J, Fantoni A, Hack C E. *Blood* 1997; 90:1501-1507.
[43] Van Molle W. Denecker G, Rodriguez I, Brouckaert P, Vandenabeele P, Libert C. *J Immunol* 1999; 163:5235-5241.
[44] Durr R, Caselmann W H. *Arch Surg* 2000; 385(3):154-161.
[45] Theal R M, Scott K. *Am Family Physician* 1996; 53:2111-2119.
[46] Ortiz-Pallardo M E, Zhou H, Fischer H P, Neuhaus T, Sachinidis A, Vetter H et al. *J Mol Med* 2000; 78:212-216.
[47] Novoradovskaya N, Lee J, Yu Z X, Ferrans V J, Brantly M. *J Clin Invest* 1998; 1:2693-2701.
[48] Tung B Y, Kowdley K V. *Gastrenterologist* 1996; 4:245-261.
[49] Wang J C. *Annu Rev Biochem* 1996; 373:635-692.
[50] Caron P R, Wang J C. in: Andoh T, Ikeda H, Oguro M. (Eds) *Molecular Biology of DNA Topoisomerases.* Boca Raton, Fla.: CRC Press, 1993: 243-263.
[51] Watanuki A, Ohwada S, Fukusato T, Makita F, Yamada T, Kikuchi A et al. *Anticancer Res* 2002; 65:1113-1119.
[52] Dingemans A C, van Ark-Otte J, Span S, Scagliotti G V, van der Valk P, Postmus P E et al. *Lung Cancer* 2001; 32:117-128.
[53] Dingemans A C, Witlox M A, Stallaert R A, van der Valk P, Postmus P E, Giaccone G. *Clin Cancer Res* 1999;2:2048-2058.
[54] Withoff S, van der Zee A G, de Jong S, Hollema H, Smit E F, Mulder N H et al. *Br J Cancer* 1999; 79:748-753.
[55] Zhou R, Wang Y, Gruber A, Larsson R, Castanos-Velez E, Liliemark E. *Med Oncol* 1999; 16:191-198.

TABLE 1

Summary of HBV-infected serum samples used. NIS refers to necroinflammatory score.

| Patients | Age | Sex | HBeAg | HBV-DNA | ALT | NIS |
|---|---|---|---|---|---|---|
| Group 1 | | | | | | |
| 1 | 41 | M | + | 5874 | 46 | 2 |
| 2 | 24 | M | + | 4032 | 21 | 1 |
| 3 | 22 | F | + | 10536 | 24 | 2 |
| 4 | 22 | M | + | 6876 | 52 | 2 |
| 5 | 44 | F | + | 6949 | 16 | 2 |
| 6 | 25 | M | + | 7443 | 36 | 1 |
| 7 | 34 | F | + | 6690 | 17 | 2 |
| 8 | 42 | M | + | 5408 | 45 | 2 |
| 9 | 50 | F | + | 5175 | 19 | 1 |
| Group 2 | | | | | | |
| 10 | 21 | F | + | 104 | 425 | 8 |
| 11 | 49 | F | + | 13 | 706 | 9 |
| 12 | 29 | F | + | 16 | 461 | 7 |
| 13 | 18 | M | + | 750 | 1050 | 8 |
| 14 | 29 | M | + | 476 | 277 | 9 |
| 15 | 31 | F | + | 454 | 307 | 7 |
| 16 | 54 | M | + | 4695 | 190 | 8 |
| 17 | 36 | M | + | 1320 | 200 | 7 |
| 18 | 49 | M | + | 471 | 253 | 7 |

TABLE 2

Summary of protein alterations in HBV infection serum samples (N/D: non-detectable)

| Protein | Area | Experimental MW(kDa)/pI | Normal (% vol) | LNS (% vol) | HNS (% vol) |
|---|---|---|---|---|---|
| Haptoglobin β chain (7 spots) | 1 | 37.2/5.0-5.6 | 3.242 ± 1.021 | 3.196 ± 1.243 | 0.873 ± 0.661 |
| Haptoglobin cleaved β chain (6 spots) | 1 | 35.7/5.1-5.8 | 0.329 ± 0.185 | 0.410 ± 0.262 | 0.066 ± 0.072 |
| Haptoglobin α2 chain (3 spots) | 2 | 19.8/5.3-5.9 | 1.225 ± 0.582 | 1.638 ± 0.631 | 0.421 ± 0.310 |
| Apo A-I (isoform 1, 2 and 3) | 3 | 23.8/5.1-5.2 | 0.136 ± 0.082 | 0.416 ± 0.179 | 0.359 ± 0.220 |
| | | | 0.708 ± 0.189 | 0.745 ± 0.256 | 0.720 ± 0.358 |
| | | | 2.893 ± 0.424 | 1.210 ± 0.401 | 1.326 ± 0.718 |
| Apo A-I fragments (10 spots) | 3 | 22.3/5.0-5.1 | 0.037 ± 0.031 | 1.043 ± 0.622 | 0.474 ± 0.284 |
| | 4 | 15.8/5.0 | N/D | 0.264 ± 0.125 | 0.163 ± 0.187 |
| Apo A-IV | 4 | 15.7/5.0 | N/D | 0.552 ± 0.335 | 0.403 ± 0.277 |
| Transthyretin | 4 | 15.9/5.1 | 0.493 ± 0.198 | 0.234 ± 0.216 | 0.237 ± 0.240 |
| α 1-Antitrypsin (normal) | | 54.4/5.0-5.2 | 2.935 ± 0.592 | 2.352 ± 0.825 | 2.384 ± 1.182 |
| α 1-Antitrypsin (fragments or isoforms) | 5 | 38.9/4.6-4.7 | 0.012 ± 0.008 | 0.524 ± 0.352 | 0.522 ± 0.484 |
| | 6 | 38.2/5.4 | N/D | 0.063 ± 0.075 | 0.170 ± 0.152 |
| | 6 | 38.2/5.6 | N/D | 0.059 ± 0.041 | 0.183 ± 0.131 |
| DNA Topoisomerase IIβ (5 spots) | 7 | 21.2/6.6-7.7 | 0.053 ± 0.027 | 0.937 ± 0.721 | 1.106 ± 0.664 |

We claim:

1. A method for detecting the presence of Hepatitis B Virus (HBV) infection in a patient being tested for HBV infection, comprising:

obtaining a serum sample from the patient;

subjecting the sample to 2D protein gel electrophoresis to separate proteins contained therein on a 2D electrophoresis gel;

staining proteins separated on the electrophoresis gel;

scanning the image of stained proteins into an image analysis scanner to obtain an image of serum protein expression profile; and comparing the serum protein expression profile consisting of apolipoprotein A-I (apoA-I), apolipoprotein A-I fragments, haptoglobin β chain, haptoglobin cleaved β-chain, haptoglobin 2 chain, apolipoprotein A-IV (apoA-IV), transthyretin, α1-anitrypsin, α1-antitrypsin fragments/isoforms, and DNA topoisomerases II (topo-II) obtained from said patient to the protein expression profile obtained from HBV-negative and HBV-infected patients, wherein an altered said protein expression profile compared to HBV-negative patient profiles indicates the presence of HBV infection in the patient.

* * * * *